United States Patent [19]

Shinohara

[11] Patent Number: 4,664,659
[45] Date of Patent: May 12, 1987

[54] MEDICAL DEVICE AND METHOD FOR MANUFACTURING THE SAME

[75] Inventor: Shuichi Shinohara, Fuji, Japan

[73] Assignee: Terumo Kabushiki Kaisha, Tokyo, Japan

[21] Appl. No.: 906,567

[22] Filed: Sep. 8, 1986

Related U.S. Application Data

[63] Continuation of Ser. No. 701,451, Feb. 13, 1985, abandoned, which is a continuation of Ser. No. 423,053, Sep. 24, 1982, abandoned.

[30] Foreign Application Priority Data

Mar. 12, 1982 [JP]  Japan ................................. 57-39245

[51] Int. Cl.⁴ ........................................... A61M 25/00
[52] U.S. Cl. .................................... 604/283; 604/192; 604/263
[58] Field of Search ............... 604/192, 198, 263, 264, 604/280, 283, 54, 414; 426/256, 412; 220/260; 156/244.11

[56]  References Cited

U.S. PATENT DOCUMENTS

| | | | |
|---|---|---|---|
| 3,523,530 | 8/1970 | Pagones et al. | 604/263 |
| 3,620,500 | 11/1971 | Santomieri | 604/280 |
| 3,977,403 | 8/1976 | Patel | 604/280 |
| 4,007,740 | 2/1977 | Owen | 604/263 |
| 4,029,837 | 6/1977 | Leatherman | 428/256 |
| 4,046,951 | 9/1977 | Stefanik | 428/412 |
| 4,091,811 | 5/1978 | Bates et al. | 604/263 |
| 4,167,431 | 9/1979 | Wong | 156/244.11 |
| 4,306,566 | 12/1981 | Sinko | 604/280 |
| 4,397,401 | 8/1983 | Ueno et al. | 220/260 |
| 4,402,682 | 9/1983 | Garver, Sr. et al. | 604/263 |
| 4,410,321 | 10/1983 | Pearson et al. | 604/414 |
| 4,428,494 | 1/1984 | Hirota et al. | 220/260 |
| 4,449,971 | 5/1984 | Cawood | 604/54 |
| 4,496,353 | 1/1985 | Overland et al. | 604/280 |

FOREIGN PATENT DOCUMENTS 3026974  5/1981  Fed. Rep. of Germany .

Primary Examiner—C. Fred Rosenbaum
Assistant Examiner—S. Vinyard
Attorney, Agent, or Firm—Frishauf, Holtz, Goodman & Woodward

[57]  ABSTRACT

A medical treatment device includes a first medical treatment implement such as a hollow needle, and a second medical treatment implement such as a bag. A first tubular member, such as a needle hub, is connected to the first implement. A second tubular member, such as a flexible tube, having first and second end portions is connected to the second implement at the second end portion. The first end portion of the second tubular member is joined and blocked with one end portion of the first tubular member in a superposed and liquid-tight state.

23 Claims, 11 Drawing Figures

MEDICAL DEVICE AND METHOD FOR MANUFACTURING THE SAME

This application is a continuation application of Ser. No. 701,451 filed Feb. 13, 1985, which in turn is a Continuation Application of Ser. No. 423,053 filed Sept. 24, 1982 (both abandoned).

BACKGROUND OF THE INVENTION

1. Field of the Invention

This invention relates to a medical device and a method for manufacturing the same.

2. Description of the Prior art

There is known a medical device comprising a first tubular member, for example, a hub into which a first medical implement such as a pricking needle is inserted, and a second tubular member, for example, a flexible tube to which a second medical implement such as a liquid vessel is connected. The first and second tubular members are made to communicate with each other. The first tubular member is bonded to the second tubular member by adhesive. The above-mentioned conventional medical device, in which medicine solution or body fluid runs through a tubular member extending between the first and second medical implements has the drawbacks that the adhesive applied to the junction of the first and second tubular members is carried into a medicine solution or body fluid; a solvent involved in an adhesive agent dissolves out into the medicine solution or body fluid; the adhesive agent is likely to decrease in adhesivity when affected by the medicine solution; and liquids leak therefrom.

SUMMARY OF THE INVENTION

It is accordingly an object of this invention to provide a medical device in which the tubular members are firmly bonded together in a liquid-tight state without applying a solvent type adhesive.

Another object of the invention is to provide a method for manufacturing a medical device in which the tubular members are firmly bonded together in a liquid-tight state without using a solvent type adhesive.

To attain the above-mentioned objects, a medical device according to this invention comprises:

a first medical implement;

a first tubular member having first and second end portions and connected to the first medical implement;

a second medical implement; and a second tubular member which has first and second end portions, whose first end portion communicates with the second medical implement, and whose second end portion is blocked with the first end portion of said first tubular member in a superposed and liquid-tight watertight state.

The above-mentioned medical treatment device of this invention is constructed by the steps of:

engaging the first tubular member having first and second end portions and connected to the first medical implement with the second tubular member which has first and second end portions and whose first end portion communicates with the second medical implement in such a manner that the first end portion of the first tubular member and the second end portion of the second tubular member are superposed on each other;

heating said superposed end portions, thereby causing the first end portion of the first tubular member to be blocked to the second end portion of the second tubular member; and cooling the superposed portions of the tubular members.

As used herein, the term "blocking" is defined to mean the phenomenon in which mutually contacting plastics materials are tightly bonded with each other without application of any adhesive.

BRIEF DESCRIPTION OF THE DRAWINGS

FIG. 1 illustrates a medical device according to a first embodiment of this invention. FIGS. 2A and 2B are sectional views of the first and second tubular members according to the first embodiment of the invention before they are bonded together. FIG. 3 in an enlarged sectional view of the bonded state of the first and second tubular members according to the first embodiment of the invention.

Figure 1:
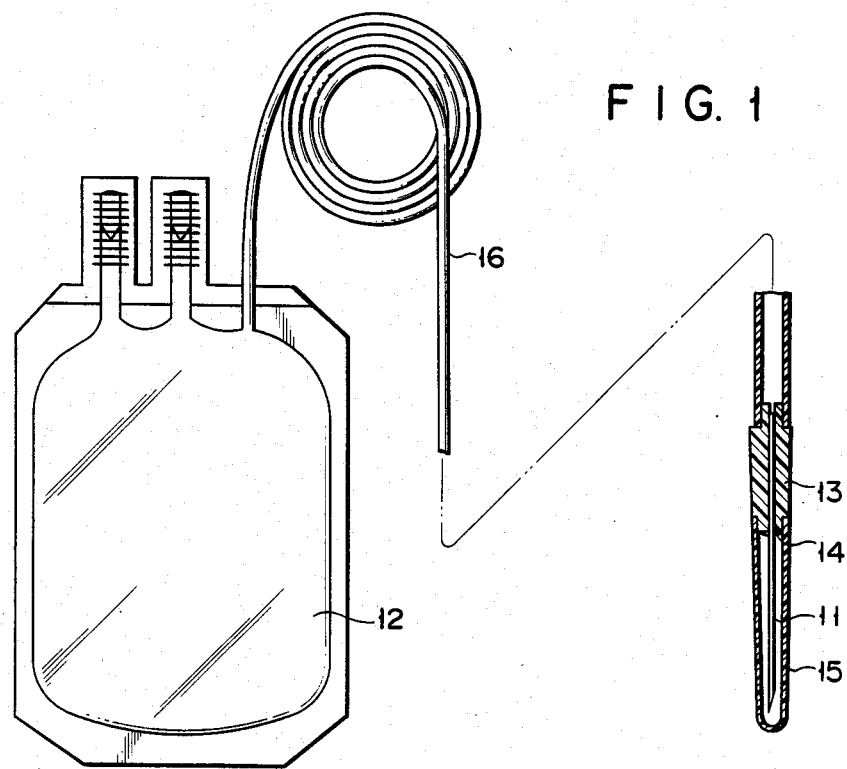
FIG. 1 illustrates a medical treatment device according to a first embodiment of this invention.

The medical device according to the first embodiment comprises a first medical implement consisting of a hollow needle 11 and a second medical implement consisting of a vessel 12. The hollow needle 11 is inserted into a hub 13 acting as the first tubular member and tightly fixed thereto by an adhesive 14. A protecter 15 is detachably fitted to the hub 13. The vessel 12 is prepared from flexible plastics material. The vessel holds therein a medical solution or a liquid such as a blood anti-coagulant aqueous solution and can be used as a transfusion bag or a blood bag. A flexible tube 16 acting as a second tubular member is connected to the vessel 12.

Figure 2A:
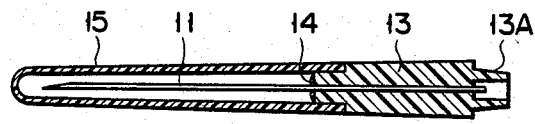
FIGS. 2A and 2B are sectional views of the first and second tubular members of the first embodiment before they are blocked together.
Figure 2B:
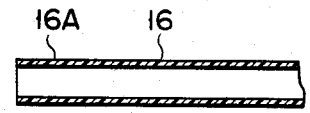

In greater detail, the hub 13 is prepared from relatively hard plastics material. As shown in FIG. 2A, that portion of the hub 13 which is joined with the tube 16 constitutes a tapered male section 13A. The tube 16 has an inner diameter substantially the same therethrough and is prepared from relatively soft plastics material. That end portion 16A of the tube 16 which is joined with the tapered male section 13A has its diameter forcefully broadened by the inserted tapered male section 13A. The tapered male section 13A of the hub 13 and the end portion 16A of the tube 16 are blocked together by a later described process in a liquid-tight or, more preferably, airtight state. The materials of the hub 13 and tube 16 should be selected from combinations which thermally give rise to blocking. Such combinations include:

| | | |
|---|---|---|
| acrylic resin | and | polyacrylic acid; |
| polyurethane | and | polyurethane; |
| polycarbonate | and | polycarbonate; |
| polyvinyl chloride | and | polyvinyl chloride; |
| polycarbonate | and | polyvinyl chloride; |
| acrylic resin | and | polyurethane; and |
| polystyrene | and | polyvinyl chloride |

Figure 3:
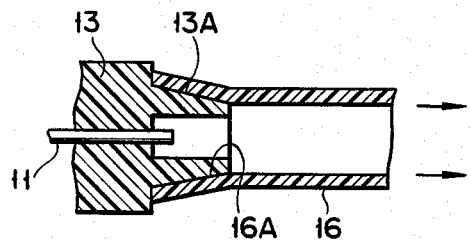
FIG. 3 is an enlarged sectional view of the bonded state of both tubular members of the first embodiment.

Description is now given of the method of manufacturing a medical device according to a first embodiment of this invention. First, the hollow needle 11 is inserted into the hub 13. The hub 13 is covered with a protector 15 to protect the hollow needle 11. A prescribed amount of a medicinal solution is introduced into the vessel 12 through that end opening of the tube 16 which is connected to the vessel 12. The tube 16 communicating at one end with the vessel 12 now filled with the medicinal solution and the hub 13 penetrated by the hollow needle 11, are tightly joined together as shown in FIG. 3 by forcing the tapered male section 13A of the hub 13 into the end portion 16A of the tube 16 with the diameter of the end portion 16A broadened. As a result, the outer periphery of the tapered male section 13A is tightly attached to the inner wall of the end portion 16A. Thereafter, the whole of the subject medical device consisting of the hollow needle 11, vessel 12, hub 13 and tube 16 is sterilized by being placed in an autoclave saturated with steam at high pressure (steam autoclaving). During the sterilization, the junction of the hub 13 and tube 16 are thermally blocked together, thereby assuring the airtight bonding of both members 13, 16. Heating required for blocking may be effected not only by means of the autoclave, but also by heater, internal heating based on high frequency waves, hot water, dry heating or placement in a hot chamber. Temperature required for blocking is usually chosen to range between 60° and 130° C. The tight blocked sections of the hub 13 and tube 16 are later allowed to cool to normal temperature.

With the aforementioned medical device according to the first embodiment of this invention, the hub 13 and tube 16 are blocked together, thereby assuring the highly liquid-tight firm bonding of both members without applying a solvent type adhesive. There is no possibility that the solvent of an adhesive dissolves out into a medicine solution. Further, even when the junction of both members happens to be brought into contact with a medicinal solution, the bonded strength of said junction is not reduced, due to freedom from an adhesive.

In contrast, the conventional medical treatment device is accompanied with the drawbacks that the used adhesive is adversely affected by a medicine solution to decrease in adhesivity; and the deposition of, for example, a medicinal solution on those portions of the aforesaid members 13, 16 which are to be bonded together often results in a failure to assure their tight bonding. In contrast, the method of this invention carries out the blocking of both members 13, 16 without application of any adhesive, thereby eliminating the occurrence of any of the above-mentioned difficulties. Moreover, according to this invention, the tube 16 is prepared from relatively soft plastics material. The tube 16 is fitted around the hub 13 in such a manner that the end portion 16A of the tube 16 has its diameter broadened by the tapered male section 13A of the hub 13. Therefore both members 13, 16 are tightly blocked together. Further, the contraction of the inner diameter of the end portion 16A of the tube 16 which results from a tensile force applied to the tube 16 assures firm blocking of both members 13, 16. The hollow needle 11 is used as a first implement, and the vessel 12 holding a liquid therein is used as a second implement, thereby enabling the subject medical device to be applied in supplying a liquid, or blood or sampling blood. The vessel 12 prepared from flexible plastics material enables the liquid to be smoothly discharged to the outside without the possibility of external air being carried into the vessel 12. If the aforementioned blocking of the tapered male section 13 and tube 16 is thermally effected in an autoclave, then said blocking and the sterilization of the whole of the subject medical device can be undertaken at the same time, elevating the productivity of said medical treatment device.

Figure 4:
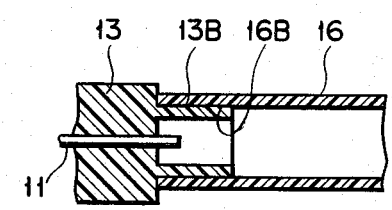
FIG. 4 is an enlarged sectional view of the blocked state of both tubular members of the second embodiment.

FIG. 4 is an enlarged sectional view of the blocked state of the tubular members included in a medical device according to a second embodiment of this invention. The second embodiment differs from the first embodiment in that the straight end portion 13B of the hub 13 is forced into the end portion 16B of the tube 16 with said end portion 16B broadened in diameter. In this case, said end portion 16B is tightly fitted due to its own contraction around the inserted straight end portion 13B of the hub 13. Subsequent application of heat enables both members 13, 16 to be effectively blocked together.

Figure 5A:
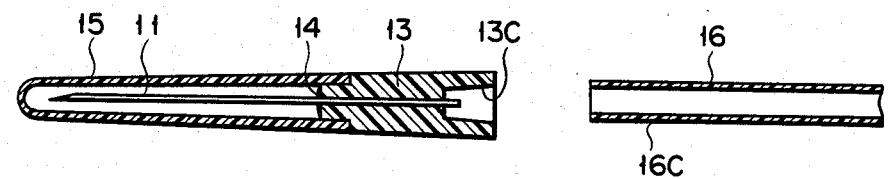
FIGS. 5A and 5B are sectional views of the first and second tubular members according to the third embodiment of the invention before they are blocked together.
Figure 5B:
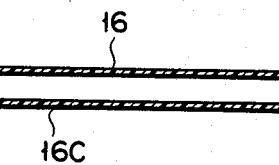
Figure 6:
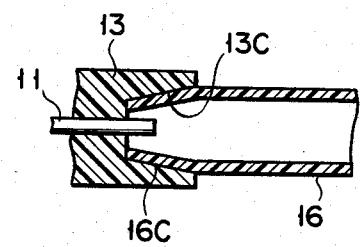
FIG. 6 is an enlarged sectional view of the blocked first and second tubular member according to the third embodiment of the invention.

FIGS. 5A and 5B are sectional views of both hub 13 and tube 16 according to a third embodiment of this invention before they are blocked together. FIG. 6 is an enlarged sectional view of the blocked state of both members 13, 16. The third embodiment differs from the first embodiment in that a female tapered end portion 13C of the hub 13 whose diameter is broadened toward the end opening, progressively contracts the diameter of the inserted end portion 16C of the tube 16. Therefore, both members 13, 16 are tightly blocked together. When the tube 16 undergoes a greater force with which the hub 13 is fitted around the tube 16, then the diameter of the end portion 16C is more easily contracted, thereby assuring the liquid-tight blocking of the end portion 16C with the tapered female section 13C.

Figure 7A:
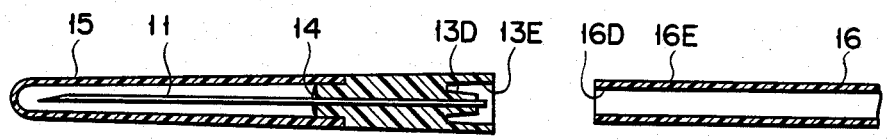
FIGS. 7A and 7B are sectional views of the first and second tubular members according to a fourth embodiment of the invention before they are blocked together.
Figure 7B:
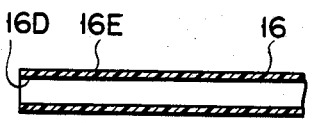
Figure 8:
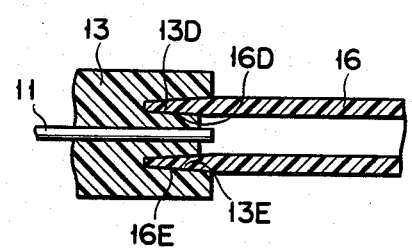
FIG. 8 is an enlarged sectional view of the blocked first and second tubular members according to the fourth embodiment of the invention.

FIGS. 7A and 7B are sectional views of the hub and tube according to a fourth most preferred embodiment of this invention, before they are blocked together. FIG. 8 is an enlarged sectional view of the blocked hub and tube according to the fourth embodiment. The fourth embodiment differs from the first embodiment in that the end portion of the hub 13 which is to be joined with the tube 16 is provided with a tapered male section 13D and an invertedly tapered female section 13E formed concentric with the male section 13D; and the inner wall 16D of the end portion of the tube 16 has its diameter broadened by the invertedly tapered male section 13D and the outer wall 16E of the end portion of the tube 16 has its diameter narrowed by the invertedly tapered female section 13E. With the medical device according to the fourth embodiment, therefore, the hub 13 and tube 16 are tightly blocked together. When a tensile force is applied to the tube 16, the end portion 16D has its diameter reduced, and firm blocking is assured by the tapered male section 13D. When the tube 16 is forced into the hub 13 with a greater force, then the outer periphery 16E of the end portion of said tube 16 is broadened. As a result the firmer blocking of the hub 13 and tube 16 is assured due to the tight contact between said broadened outer periphery and the tapered female section 13E.

This invention is not limited to a medical device comprising the first and second implements according to the aforementioned embodiments, but is applicable to any other medical device in which said first and second implements have to be tightly joined.

What is claimed is:

1. A medical device which comprises:
    a first part for conducting a liquid;
    a first tubular member of relatively hard plastics material having first and second end portions wherein the second end portion is connected to the first liquid conducting part for communicating liquid between said first liquid conducting part and said first end portion;
    a second part for conducting said liquid; and
    a second tubular member of relatively soft plastics material which has first and second end portions;
    said first and second tubular members being formed, respectively, or said second and first tubular members being formed, respectively, of
    acrylic resin and polyacrylic acid;
    polyurethane and polyurethane;
    polycarbonate and polycarbonate;
    polyvinyl chloride and polyvinyl chloride;
    polycarbonate and polyvinyl chloride;
    acrylic resin and polyurethane; or
    polystyrene and polyvinyl chloride; and
    the first end portion of said second tubular member being in communication with the second liquid conducting part, and the second end portion of said second tubular member being heat joined and firmly bonded by blocking with the first end portion of said first tubular member in a superposed state to form a strong, durable, liquid-tight joint in the absence of adhesive materials, the heat joining by blocking being accomplished during heat sterilization of the complete medical device at a temperature below the melting point of any of the plastic materials forming the medical device, the joined end portions of said first and said second tubular members being initially forcibly fitted to one another and having respective diameters such that the diameter of the second end portion of said tubular member is elastically deformed by the first end portion of said first tubular member when they are forcibly fitted to each other prior to being heated.

2. The medical device according to claim 1, wherein the joined portion of the first tubular member has a tapered male section; and the second tubular member is initially fitted with an inserted portion of said first tubular member in such a manner that the end inner diameter of said second tubular member is broadened by said tapered male section.

3. The medical device according to claim 1, wherein the joined portion of the first tubular member has an invertedly tapered female section; and the second tubular member is initially fitted with the female section of the first tubular member in such a manner that the outer diameter of the joined end of said second tubular member is reduced by said invertedly tapered female section.

4. The medical device according to claim 1, wherein the first liquid conducting part is a hollow needle projecting from said second end portion of said first tubular member, and the second liquid conducting part is a vessel for holding a liquid.

5. The medical device according to claim 1, wherein the first and second tubular members are prepared from polyvinyl chloride.

6. The medical device according to claim 6, wherein the second liquid conducting part includes liquid-holding vessel is prepared from flexible plastics material.

7. A method of manufacturing a medical device which comprises the steps of:
    joining a first tubular member of relatively hard plastics material which has first and second end portions and which is connected at its second end portion to a first part for conducting a liquid, with a second tubular member of relatively soft plastics material which has first and second end portions and which communicates with a second part for conducting said liquid at its first end portion, whereby the first end portion of the first tubular member and the second end portion of the second tubular member are superposed on each other in the absence of adhesive materials; said first and second tubular members being formed, respectively, or said second and first tubular members being formed, respectively, of
    acrylic resin and polyacrylic acid;
    polyurethane and polyurethane;
    polycarbonate and polycarbonate;
    polyvinyl chloride and polyvinyl chloride;
    polycarbonate and polyvinyl chloride;
    acrylic resin and polyurethane; or
    polystyrene and polyvinyl chloride; and
    forcibly fitting the joined end portions of the first and the second tubular members to one another, the joined end portions of said first and second tubular members having respective diameters such that when they are joined by said forcible fitting the diameter of the second end portion of the second tubular member is elastically deformed by the first end portion of the first tubular member;
    heating the superposed end portions after said fitting and deforming steps, said heating being carried out by placing the whole of the medical device in an autoclave to heat sterilize the medical device at a temperature below the melting point of any of the plastic materials forming the medical device, thereby firmly bonding the forcibly fitted first end portion of the first tubular member to the forcibly fitted deformed second end portion of the second tubular member to formed a strong, durable, liquid-tight joint only by the blocking effect produced during the heat sterilizing of said medical device; and
    cooling the superposed end portions of said first and said second tubular members.

8. The method according to claim 8, wherein the joined portion of the first tubular member has a tapered male section; and the second tubular member is fitted with an inserted portion of said first tubular member in such a manner that the end inner diameter of said second tubular member is broadened by said tapered male section.

9. The method according to claim 7, wherein the joined portion of the first tubular member has an inverted tapered female section; and the second tubular member is fitted with the female section of the first tubular member in such a manner that the outer diameter of the joined end of said second tubular member is reduced by said invertedly tapered female section.

10. The medical device according to claim 4, wherein the first and second tubular members are prepared from polyvinyl chloride.

11. The medical device according to claim 10, wherein the liquid-holding vessel is prepared from flexible plastics material.

12. The medical device according to claim 4, wherein the liquid-holding vessel is prepared from flexible plastics material.

13. The medical device according to claim 1, wherein said first tubular member is made of acrylic resin, and said second tubular member is made of polyacrylic acid.

14. The medical device according to claim 1, wherein said first and said second tubular members are made of polyurethane.

15. The medical device according to claim 1, wherein said first and said second tubular members are made of polycarbonate.

16. The medical device according to claim 1, wherein said first tubular member is made of polycarbonate and said second tubular member is made of polyvinyl chloride.

17. The medical device according to claim 1, wherein said first tubular member is made of acrylic resin, and said second tubular member is made of polyurethane.

18. The medical device according to claim 1, wherein said first tubular member is made of polystyrene, and said second tubular member is made of polyvinyl chloride.

19. A medical device which comprises:
a first part for conducting a liquid;
a first tubular member of relatively hard plastics material having first and second end portions, said second end portion of said first tubular member being connected to said first liquid conducting part for communicating liquid between said first liquid conducting part and said first end portion;
a second part for conducting said liquid; and
a second tubular member of relatively soft and self-contractible plastics material which has first and second end portions, said first end portion of said second tubular member being in communication with said second liquid conducting part;
said second end portion of said second tubular member being superposed and joined with said first end portion of said first tubular member by forcible fitting of one of said joined end portions on the other of said joined end portions, in the absence of adhesive materials, said joined end portions having respective diameters such that the diameter of the second end portion of said second tubular member is elastically deformed by the first end portion of said first tubular member prior to being heated; and
said joined end portions of said tubular members being heated to firmly bond them together by blocking, excluding fusion, with said end portions being in said joined superposed state, to form a strong, durable, liquid-tight joint in the absence of adhesive materials, the heat joining by blocking being accomplished during heat sterilization of the complete medical device including the joined portions of the medical device at a termperature below the melting point of any of the plastics materials forming the medical device.

20. The medical device according to claim 19, wherein said second tubular member has a vessel for transfusion liquid or blood connected thereto.

21. The medical device according to claim 20, wherein said vessel contains transfusion liquid.

22. The medical device according to claim 19, wherein said heat sterilization is conducted at a temperature of 60° to 130° C.

23. The medical device according to claim 22, wherein said heat sterilization is performed in an autoclave.

* * * * *

UNITED STATES PATENT AND TRADEMARK OFFICE
CERTIFICATE OF CORRECTION

PATENT NO. : 4,664,659

DATED : May 12, 1987

INVENTOR(S) : S. SHINOHARA

It is certified that error appears in the above-identified patent and that said Letters Patent is hereby corrected as shown below:

Column 2, between lines 35 and 36, insert the heading
-- Detailed Description of the Preferred Embodiments -- .

Column 6, line 6 (Claim 6), "according to claim 6" should read -- according to claim 5 -- .

Column 6, line 8 (Claim 6), delete the word "is".

Column 6, line 57 (Claim 8), "according to claim 8" should read -- according to claim 7 -- .

Signed and Sealed this

Twenty-sixth Day of January, 1988

*Attest:*

DONALD J. QUIGG

*Attesting Officer*     *Commissioner of Patents and Trademarks*